(12) United States Patent
Copt et al.

(10) Patent No.: US 11,211,043 B2
(45) Date of Patent: Dec. 28, 2021

(54) AUDIO ENHANCED HEARING PROTECTION SYSTEM (71) Applicant: Bongiovi Acoustics LLC, Port St. Lucie, FL (US)

(72) Inventors: Ryan J. Copt, Port St. Lucie, FL (US); Joseph G. Butera, III, Stuart, FL (US); Robert J. Summers, III, Port St. Lucie, FL (US); Mark Harpster, Port St. Lucie, FL (US)

(73) Assignee: Bongiovi Acoustics LLC, Port St. Lucie, FL (US)

( * ) Notice: Subject to any disclaimer, the term of this patent is extended or adjusted under 35 U.S.C. 154(b) by 0 days.

(21) Appl. No.: 16/381,659

(22) Filed: Apr. 11, 2019

(65) Prior Publication Data
US 2019/0318719 A1 Oct. 17, 2019

Related U.S. Application Data (60) Provisional application No. 62/656,150, filed on Apr. 11, 2018.

(51) Int. Cl.
*A61F 11/14* (2006.01)
*G10K 11/178* (2006.01)
*H04R 1/10* (2006.01)

(52) U.S. Cl.
CPC ........ *G10K 11/17823* (2018.01); *A61F 11/14* (2013.01); *H04R 1/1008* (2013.01);
(Continued)

(58) Field of Classification Search
CPC .... A61F 11/12; A61F 11/14; A61F 2011/145; G10K 11/17823; G10K 11/17861;
(Continued)

(56) References Cited

U.S. PATENT DOCUMENTS

| 2,643,729 A | 6/1953 | McCracken |
| 3,430,007 A | 2/1969 | Thielen |

(Continued)

FOREIGN PATENT DOCUMENTS

| BR | 9611417 | 2/1999 |
| BR | 96113723 | 7/1999 |

(Continued)

OTHER PUBLICATIONS

NovaSound Int., http://www.novasoundint.com/new_page_t.htm, 2004.
(Continued)

*Primary Examiner* — Vivian C Chin
*Assistant Examiner* — Friedrich Fahnert
(74) *Attorney, Agent, or Firm* — Malloy & Malloy, PL (57) ABSTRACT

An audio enhanced hearing protection system to be worn by a user includes an ambient noise reduction assembly having a primary noise reduction unit and a secondary noise reduction unit. The audio enhanced hearing protection system also includes an audio input assembly having one or more environmental microphones to receive raw environmental audio signals. The raw audio signals are transformed into processed audio signals via a digital signal processing assembly prior to transmission to a user. The audio enhanced hearing protection system also includes an audio output assembly having at least one speaker to transmit processed audio signals to a user.

13 Claims, 5 Drawing Sheets

(52) U.S. Cl.
CPC ...... *H04R 1/1083* (2013.01); *A61F 2011/145* (2013.01); *G10K 2210/1081* (2013.01); *G10K 2210/3046* (2013.01); *G10K 2210/3224* (2013.01)

(58) Field of Classification Search
CPC ..... G10K 11/17873; G10K 2210/1081; G10K 2210/3046; G10K 2210/3224; H04R 1/1008; H04R 1/1016; H04R 1/1083; H04R 2201/107; H04R 2420/07; H04R 2460/01
USPC ....... 381/55, 71.1, 71.6, 71.7, 71.8, 72, 374, 381/375, 376, 377, 378, 379
See application file for complete search history.

(56) References Cited

U.S. PATENT DOCUMENTS

| | | |
|---|---|---|
| 3,795,876 A | 3/1974 | Takashi et al. |
| 3,813,687 A | 5/1974 | Geil |
| 4,162,462 A | 7/1979 | Endoh et al. |
| 4,184,047 A | 1/1980 | Langford |
| 4,218,950 A | 8/1980 | Uetrecht |
| 4,226,533 A | 10/1980 | Snowman |
| 4,257,325 A | 3/1981 | Bertagni |
| 4,353,035 A | 10/1982 | Schröder |
| 4,356,558 A | 10/1982 | Owen et al. |
| 4,363,007 A | 12/1982 | Haramoto et al. |
| 4,392,027 A | 7/1983 | Bock |
| 4,399,474 A | 8/1983 | Coleman, Jr. |
| 4,412,100 A | 10/1983 | Orban |
| 4,458,362 A | 7/1984 | Berkovitz et al. |
| 4,489,280 A | 12/1984 | Bennett, Jr. et al. |
| 4,517,415 A | 5/1985 | Laurence |
| 4,538,297 A | 8/1985 | Waller |
| 4,549,289 A | 10/1985 | Schwartz et al. |
| 4,584,700 A | 4/1986 | Scholz |
| 4,602,381 A | 7/1986 | Cugnini et al. |
| 4,612,665 A | 9/1986 | Inami et al. |
| 4,641,361 A | 2/1987 | Rosback |
| 4,677,645 A | 6/1987 | Kaniwa et al. |
| 4,696,044 A | 9/1987 | Waller, Jr. |
| 4,701,953 A | 10/1987 | White |
| 4,704,726 A | 11/1987 | Gibson |
| 4,715,559 A | 12/1987 | Fuller |
| 4,739,514 A | 4/1988 | Short et al. |
| 4,768,380 A | 9/1988 | Vermeiren et al. |
| 4,815,142 A | 3/1989 | Imreh |
| 4,856,068 A | 8/1989 | Quatieri, Jr. et al. |
| 4,887,299 A | 12/1989 | Cummins et al. |
| 4,997,058 A | 3/1991 | Bertagni |
| 5,007,707 A | 4/1991 | Bertagni |
| 5,073,936 A | 12/1991 | Gurike et al. |
| 5,133,015 A | 7/1992 | Scholz |
| 5,195,141 A | 3/1993 | Jang |
| 5,210,704 A | 5/1993 | Husseiny |
| 5,210,806 A | 5/1993 | Kihara et al. |
| 5,226,076 A * | 7/1993 | Baumhauer, Jr. ........ H04M 1/19 379/419 |
| 5,355,417 A | 10/1994 | Burdisso et al. |
| 5,361,381 A | 11/1994 | Short |
| 5,384,856 A | 1/1995 | Kyouno et al. |
| 5,420,929 A | 5/1995 | Geddes et al. |
| 5,425,107 A | 6/1995 | Bertagni et al. |
| 5,463,695 A | 10/1995 | Werrbach |
| 5,465,421 A | 11/1995 | McCormick et al. |
| 5,467,775 A | 11/1995 | Callahan et al. |
| 5,473,214 A | 12/1995 | Hildebrand |
| 5,511,129 A | 4/1996 | Craven et al. |
| 5,515,444 A | 5/1996 | Burdisso et al. |
| 5,539,835 A | 7/1996 | Bertagni et al. |
| 5,541,866 A | 7/1996 | Sato et al. |
| 5,572,443 A | 11/1996 | Emoto et al. |
| 5,615,275 A | 3/1997 | Bertagni |
| 5,617,480 A | 4/1997 | Ballard et al. |
| 5,638,456 A | 6/1997 | Conley et al. |
| 5,640,685 A | 6/1997 | Komoda |
| 5,671,287 A | 9/1997 | Gerzon |
| 5,693,917 A | 12/1997 | Bertagni et al. |
| 5,699,438 A | 12/1997 | Smith et al. |
| 5,727,074 A | 3/1998 | Hildebrand |
| 5,737,432 A | 4/1998 | Werrbach |
| 5,812,684 A | 9/1998 | Mark |
| 5,828,768 A | 10/1998 | Eatwell et al. |
| 5,832,097 A | 11/1998 | Armstrong et al. |
| 5,838,805 A | 11/1998 | Warnaka et al. |
| 5,848,164 A | 12/1998 | Levine |
| 5,861,686 A | 1/1999 | Lee |
| 5,862,461 A | 1/1999 | Yoshizawa et al. |
| 5,872,852 A | 2/1999 | Dougherty |
| 5,901,231 A | 5/1999 | Parrella et al. |
| 5,990,955 A | 11/1999 | Koz |
| 6,058,196 A | 5/2000 | Heron |
| 6,078,670 A | 6/2000 | Beyer |
| 6,093,144 A | 7/2000 | Jaeger et al. |
| 6,108,431 A | 8/2000 | Bachler |
| 6,195,438 B1 | 2/2001 | Yumoto et al. |
| 6,201,873 B1 | 3/2001 | Dal Farra |
| 6,202,601 B1 | 3/2001 | Ouellette et al. |
| 6,208,237 B1 | 3/2001 | Saiki et al. |
| 6,244,376 B1 | 6/2001 | Granzotto |
| 6,263,354 B1 | 7/2001 | Gandhi |
| 6,285,767 B1 | 9/2001 | Klayman |
| 6,292,511 B1 | 9/2001 | Goldston et al. |
| 6,317,117 B1 | 11/2001 | Goff |
| 6,318,797 B1 | 11/2001 | Böhm et al. |
| 6,332,029 B1 | 12/2001 | Azima et al. |
| 6,343,127 B1 | 1/2002 | Billoud |
| 6,484,845 B1 | 11/2002 | Schleicher et al. |
| 6,518,852 B1 | 2/2003 | Derrick |
| 6,529,611 B2 | 3/2003 | Kobayashi et al. |
| 6,535,846 B1 | 3/2003 | Shashoua |
| 6,570,993 B1 | 5/2003 | Fukuyama |
| 6,587,564 B1 | 7/2003 | Cusson |
| 6,618,487 B1 | 9/2003 | Azima et al. |
| 6,661,897 B2 | 12/2003 | Smith |
| 6,661,900 B1 | 12/2003 | Allred et al. |
| 6,760,451 B1 | 7/2004 | Craven et al. |
| 6,772,114 B1 | 8/2004 | Sluijter et al. |
| 6,839,438 B1 | 1/2005 | Riegelsberger et al. |
| 6,847,258 B2 | 1/2005 | Ishida et al. |
| 6,871,525 B2 | 3/2005 | Withnall et al. |
| 6,907,391 B2 | 6/2005 | Bellora et al. |
| 6,999,826 B1 | 2/2006 | Zhou et al. |
| 7,006,653 B2 | 2/2006 | Guenther |
| 7,016,746 B2 | 3/2006 | Wiser et al. |
| 7,024,001 B1 | 4/2006 | Nakada |
| 7,058,463 B1 | 6/2006 | Ruha et al. |
| 7,123,728 B2 | 10/2006 | King et al. |
| 7,236,602 B2 | 6/2007 | Gustavsson |
| 7,254,243 B2 | 8/2007 | Bongiovi |
| 7,266,205 B2 | 9/2007 | Miller |
| 7,269,234 B2 | 9/2007 | Klingenbrunn et al. |
| 7,274,795 B2 | 9/2007 | Bongiovi |
| 7,430,300 B2 * | 9/2008 | Vosburgh ................ H04S 1/002 181/129 |
| 7,519,189 B2 | 4/2009 | Bongiovi |
| 7,577,263 B2 | 8/2009 | Tourwe |
| 7,613,314 B2 | 11/2009 | Camp, Jr. |
| 7,676,048 B2 | 3/2010 | Tsutsui |
| 7,711,129 B2 | 5/2010 | Lindahl |
| 7,711,442 B2 | 5/2010 | Ryle et al. |
| 7,747,447 B2 | 6/2010 | Christensen et al. |
| 7,764,802 B2 | 7/2010 | Oliver |
| 7,778,718 B2 | 8/2010 | Janke et al. |
| 7,916,876 B1 | 3/2011 | Helsloot |
| 8,068,621 B2 | 11/2011 | Okabayashi et al. |
| 8,144,902 B2 | 3/2012 | Johnston |
| 8,160,274 B2 | 4/2012 | Bongiovi |
| 8,175,287 B2 | 5/2012 | Ueno et al. |
| 8,218,789 B2 | 7/2012 | Bharitkar et al. |
| 8,229,136 B2 | 7/2012 | Bongiovi |
| 8,284,955 B2 | 10/2012 | Bongiovi et al. |
| 8,385,864 B2 | 2/2013 | Dickson et al. |

(56) References Cited

U.S. PATENT DOCUMENTS

| | | |
|---|---|---|
| 8,462,963 B2 | 6/2013 | Bongiovi |
| 8,472,642 B2 | 6/2013 | Bongiovi |
| 8,503,701 B2 | 8/2013 | Miles et al. |
| 8,565,449 B2 | 10/2013 | Bongiovi |
| 8,577,676 B2 | 11/2013 | Muesch |
| 8,619,998 B2 | 12/2013 | Walsh et al. |
| 8,705,765 B2 | 4/2014 | Bongiovi |
| 8,750,538 B2 | 6/2014 | Avendano et al. |
| 8,811,630 B2 | 8/2014 | Burlingame |
| 8,879,743 B1 | 11/2014 | Mitra |
| 9,195,433 B2 | 11/2015 | Bongiovi et al. |
| 9,264,004 B2 | 2/2016 | Bongiovi et al. |
| 9,276,542 B2 | 3/2016 | Bongiovi et al. |
| 9,281,794 B1 | 3/2016 | Bongiovi et al. |
| 9,344,828 B2 | 5/2016 | Bongiovi et al. |
| 9,348,904 B2 | 5/2016 | Bongiovi et al. |
| 9,350,309 B2 | 5/2016 | Bongiovi et al. |
| 9,397,629 B2 | 7/2016 | Bongiovi et al. |
| 9,398,394 B2 | 7/2016 | Bongiovi et al. |
| 9,413,321 B2 | 8/2016 | Bongiovi et al. |
| 9,564,146 B2 | 2/2017 | Bongiovi et al. |
| 9,615,189 B2 | 4/2017 | Copt et al. |
| 9,621,994 B1 | 4/2017 | Bongiovi et al. |
| 9,638,672 B2 | 5/2017 | Butera, III et al. |
| 9,741,355 B2 | 8/2017 | Bongiovi et al. |
| 9,793,872 B2 | 10/2017 | Bongiovi et al. |
| 9,883,318 B2 | 1/2018 | Bongiovi et al. |
| 9,906,858 B2 | 2/2018 | Bongiovi et al. |
| 9,906,867 B2 | 2/2018 | Bongiovi et al. |
| 9,998,832 B2 | 6/2018 | Bongiovi et al. |
| 10,069,471 B2 | 9/2018 | Bongiovi et al. |
| 10,158,337 B2 | 12/2018 | Bongiovi et al. |
| 10,666,216 B2 | 5/2020 | Bongiovi et al. |
| 10,701,505 B2 | 6/2020 | Copt et al. |
| 10,959,035 B2 | 3/2021 | Butera, III et al. |
| 10,999,695 B2 | 5/2021 | Bongiovi et al. |
| 2001/0008535 A1 | 7/2001 | Lanigan |
| 2001/0043704 A1 | 11/2001 | Schwartz |
| 2001/0046304 A1 | 11/2001 | Rast |
| 2002/0057808 A1 | 5/2002 | Goldstein |
| 2002/0071481 A1 | 6/2002 | Goodings |
| 2002/0094096 A1 | 7/2002 | Paritsky et al. |
| 2003/0016838 A1 | 1/2003 | Paritsky et al. |
| 2003/0023429 A1 | 1/2003 | Claesson et al. |
| 2003/0035555 A1 | 2/2003 | King et al. |
| 2003/0043940 A1 | 3/2003 | Janky et al. |
| 2003/0112088 A1 | 6/2003 | Bizjak |
| 2003/0138117 A1 | 7/2003 | Goff |
| 2003/0142841 A1 | 7/2003 | Wiegand |
| 2003/0164546 A1 | 9/2003 | Giger |
| 2003/0179891 A1 | 9/2003 | Rabinowitz et al. |
| 2003/0216907 A1 | 11/2003 | Thomas |
| 2004/0003805 A1 | 1/2004 | Ono |
| 2004/0005063 A1 | 1/2004 | Klayman |
| 2004/0008851 A1 | 1/2004 | Hagiwara |
| 2004/0022400 A1 | 2/2004 | Magrath |
| 2004/0042625 A1 | 3/2004 | Brown |
| 2004/0044804 A1 | 3/2004 | Mac Farlane |
| 2004/0086144 A1 | 5/2004 | Kallen |
| 2004/0103588 A1 | 6/2004 | Allaei |
| 2004/0138769 A1 | 7/2004 | Akiho |
| 2004/0146170 A1 | 7/2004 | Zint |
| 2004/0189264 A1 | 9/2004 | Matsuura et al. |
| 2004/0208646 A1 | 10/2004 | Choudhary et al. |
| 2005/0013453 A1 | 1/2005 | Cheung |
| 2005/0090295 A1 | 4/2005 | Ali et al. |
| 2005/0117771 A1 | 6/2005 | Vosburgh et al. |
| 2005/0129248 A1 | 6/2005 | Kraemer et al. |
| 2005/0175185 A1 | 8/2005 | Korner |
| 2005/0201572 A1 | 9/2005 | Lindahl et al. |
| 2005/0249272 A1 | 11/2005 | Kirkeby et al. |
| 2005/0254564 A1 | 11/2005 | Tsutsui |
| 2006/0034467 A1 | 2/2006 | Sleboda et al. |
| 2006/0045294 A1 | 3/2006 | Smyth |
| 2006/0064301 A1 | 3/2006 | Aguilar et al. |
| 2006/0098827 A1 | 5/2006 | Paddock et al. |
| 2006/0115107 A1 | 6/2006 | Vincent et al. |
| 2006/0126851 A1 | 6/2006 | Yuen et al. |
| 2006/0126865 A1 | 6/2006 | Blamey et al. |
| 2006/0138285 A1 | 6/2006 | Oleski et al. |
| 2006/0140319 A1 | 6/2006 | Eldredge et al. |
| 2006/0153281 A1 | 7/2006 | Karlsson |
| 2006/0189841 A1 | 8/2006 | Pluvinage |
| 2006/0291670 A1 | 12/2006 | King et al. |
| 2007/0010132 A1 | 1/2007 | Nelson |
| 2007/0030994 A1 | 2/2007 | Ando et al. |
| 2007/0056376 A1 | 3/2007 | King |
| 2007/0106179 A1 | 5/2007 | Bagha et al. |
| 2007/0119421 A1 | 5/2007 | Lewis et al. |
| 2007/0150267 A1 | 6/2007 | Honma et al. |
| 2007/0173990 A1 | 7/2007 | Smith et al. |
| 2007/0177459 A1 | 8/2007 | Behn |
| 2007/0206643 A1 | 9/2007 | Egan |
| 2007/0223713 A1 | 9/2007 | Gunness |
| 2007/0223717 A1 | 9/2007 | Boersma |
| 2007/0253577 A1 | 11/2007 | Yen et al. |
| 2008/0031462 A1 | 2/2008 | Walsh et al. |
| 2008/0040116 A1 | 2/2008 | Cronin |
| 2008/0049948 A1 | 2/2008 | Christoph |
| 2008/0069385 A1 | 3/2008 | Revit |
| 2008/0123870 A1 | 5/2008 | Stark |
| 2008/0123873 A1 | 5/2008 | Bjorn-Josefsen et al. |
| 2008/0165989 A1 | 7/2008 | Seil et al. |
| 2008/0181424 A1 | 7/2008 | Schulein et al. |
| 2008/0212798 A1 | 9/2008 | Zartarian |
| 2008/0255855 A1 | 10/2008 | Lee et al. |
| 2009/0022328 A1 | 1/2009 | Neugebauer et al. |
| 2009/0054109 A1 | 2/2009 | Hunt |
| 2009/0080675 A1 | 3/2009 | Smirnov et al. |
| 2009/0086996 A1 | 4/2009 | Bongiovi et al. |
| 2009/0282810 A1 | 11/2009 | Leone et al. |
| 2009/0290725 A1 | 11/2009 | Huang |
| 2009/0296959 A1 | 12/2009 | Bongiovi |
| 2010/0008530 A1 | 1/2010 | Hlas et al. |
| 2010/0045374 A1 | 2/2010 | Wu et al. |
| 2010/0246832 A1 | 9/2010 | Villemoes et al. |
| 2010/0252677 A1 | 10/2010 | Petitjean |
| 2010/0256843 A1 | 10/2010 | Bergstein et al. |
| 2010/0278364 A1 | 11/2010 | Berg |
| 2010/0303278 A1 | 12/2010 | Sahyoun |
| 2011/0002467 A1 | 1/2011 | Nielsen |
| 2011/0007907 A1* | 1/2011 | Park .............. G10K 11/178 381/71.8 |
| 2011/0013736 A1 | 1/2011 | Tsukamoto et al. |
| 2011/0065408 A1 | 3/2011 | Kenington et al. |
| 2011/0087346 A1 | 4/2011 | Larsen et al. |
| 2011/0096936 A1 | 4/2011 | Gass |
| 2011/0125063 A1 | 5/2011 | Shalon et al. |
| 2011/0194712 A1 | 8/2011 | Potard |
| 2011/0230137 A1 | 9/2011 | Hicks et al. |
| 2011/0257833 A1 | 10/2011 | Trush et al. |
| 2011/0280411 A1 | 11/2011 | Cheah et al. |
| 2012/0008798 A1 | 1/2012 | Ong |
| 2012/0014553 A1 | 1/2012 | Bonanno |
| 2012/0020502 A1 | 1/2012 | Adams |
| 2012/0022842 A1 | 1/2012 | Amadu |
| 2012/0063611 A1 | 3/2012 | Kimura |
| 2012/0089045 A1 | 4/2012 | Seidl et al. |
| 2012/0099741 A1 | 4/2012 | Gotoh et al. |
| 2012/0170759 A1 | 7/2012 | Yuen et al. |
| 2012/0170795 A1 | 7/2012 | Sancisi et al. |
| 2012/0189131 A1 | 7/2012 | Ueno et al. |
| 2012/0213034 A1 | 8/2012 | Imran |
| 2012/0213375 A1 | 8/2012 | Mahabub et al. |
| 2012/0300949 A1 | 11/2012 | Rauhala |
| 2012/0302920 A1 | 11/2012 | Bridger et al. |
| 2013/0083958 A1 | 4/2013 | Katz et al. |
| 2013/0089225 A1 | 4/2013 | Tsai |
| 2013/0129106 A1 | 5/2013 | Sapiejewski |
| 2013/0162908 A1 | 6/2013 | Son et al. |
| 2013/0163767 A1* | 6/2013 | Gauger, Jr. .......... H04R 1/1083 381/55 |
| 2013/0163783 A1 | 6/2013 | Burlingame |
| 2013/0169779 A1 | 7/2013 | Pedersen |

(56) References Cited

U.S. PATENT DOCUMENTS

| | | | |
|---|---|---|---|
| 2013/0220274 A1 | 8/2013 | Deshpande et al. | |
| 2013/0227631 A1 | 8/2013 | Sharma et al. | |
| 2013/0242191 A1 | 9/2013 | Leyendecker | |
| 2013/0251175 A1 | 9/2013 | Bongiovi et al. | |
| 2013/0288596 A1 | 10/2013 | Suzuki et al. | |
| 2013/0338504 A1 | 12/2013 | Demos et al. | |
| 2013/0343564 A1* | 12/2013 | Darlington | H04R 1/1083 381/74 |
| 2014/0067236 A1 | 3/2014 | Henry et al. | |
| 2014/0119583 A1 | 5/2014 | Valentine et al. | |
| 2014/0126734 A1 | 5/2014 | Gauger, Jr. et al. | |
| 2014/0257714 A1 | 9/2014 | Kiviniemi et al. | |
| 2014/0261301 A1 | 9/2014 | Leone | |
| 2014/0379355 A1 | 12/2014 | Hosokawsa | |
| 2015/0039250 A1 | 2/2015 | Rank | |
| 2015/0208163 A1 | 7/2015 | Hallberg et al. | |
| 2015/0215720 A1 | 7/2015 | Carroll | |
| 2016/0209831 A1 | 7/2016 | Pal | |
| 2017/0072305 A1 | 3/2017 | Watanabe | |
| 2017/0188989 A1 | 7/2017 | Copt et al. | |
| 2017/0193980 A1 | 7/2017 | Bongiovi et al. | |
| 2017/0195802 A1 | 7/2017 | Eichfeld et al. | |
| 2017/0208380 A1* | 7/2017 | Slater | H04R 1/1016 |
| 2017/0241422 A1 | 8/2017 | Munk et al. | |
| 2017/0272887 A1 | 9/2017 | Copt et al. | |
| 2017/0345408 A1 | 11/2017 | Hong et al. | |
| 2018/0077482 A1* | 3/2018 | Yuan | H04R 1/08 |
| 2018/0091109 A1 | 3/2018 | Bongiovi et al. | |
| 2018/0102133 A1 | 4/2018 | Bongiovi et al. | |
| 2018/0139565 A1 | 5/2018 | Norris et al. | |
| 2018/0213343 A1 | 7/2018 | Copt et al. | |
| 2018/0226064 A1* | 8/2018 | Seagriff | H04L 63/0428 |
| 2019/0020950 A1 | 1/2019 | Bongiovi et al. | |
| 2019/0069114 A1 | 2/2019 | Tai et al. | |
| 2019/0075388 A1* | 3/2019 | Schrader | H04R 1/1041 |
| 2019/0318719 A1 | 10/2019 | Bongiovi et al. | |
| 2019/0387340 A1 | 12/2019 | Audfray et al. | |
| 2020/0007983 A1 | 1/2020 | Bongiovi et al. | |
| 2020/0053503 A1 | 2/2020 | Butera, III et al. | |
| 2020/0404441 A1 | 12/2020 | Copt et al. | |
| 2021/0152937 A1 | 5/2021 | Bongiovi et al. | |
| 2021/0257983 A1 | 8/2021 | Bongiovi et al. | |

FOREIGN PATENT DOCUMENTS

| | | |
|---|---|---|
| CA | 2533221 | 6/1995 |
| CA | 2161412 | 4/2000 |
| CA | 2854086 | 12/2018 |
| CN | 1139842 | 1/1997 |
| CN | 1173268 A | 2/1998 |
| CN | 1221528 A | 6/1999 |
| CN | 1243653 | 2/2000 |
| CN | 1357136 A | 7/2002 |
| CN | 1391780 | 1/2003 |
| CN | 1682567 | 10/2005 |
| CN | 1879449 | 12/2006 |
| CN | 1910816 A | 2/2007 |
| CN | 101163354 | 4/2008 |
| CN | 101277331 | 10/2008 |
| CN | 101518083 | 8/2009 |
| CN | 101536541 A | 9/2009 |
| CN | 101720557 | 6/2010 |
| CN | 101946526 A | 1/2011 |
| CN | 101964189 | 2/2011 |
| CN | 102171755 | 8/2011 |
| CN | 102265641 | 11/2011 |
| CN | 102361506 | 2/2012 |
| CN | 102498729 | 6/2012 |
| CN | 102652337 | 8/2012 |
| CN | 102754151 | 10/2012 |
| CN | 102822891 | 12/2012 |
| CN | 102855882 | 1/2013 |
| CN | 103004237 A | 3/2013 |
| CN | 103141121 | 6/2013 |
| CN | 203057339 | 7/2013 |
| CN | 103247297 | 8/2013 |
| CN | 103250209 | 8/2013 |
| CN | 103262577 | 8/2013 |
| CN | 103348697 | 10/2013 |
| CN | 103455824 | 12/2013 |
| CN | 1672325 | 9/2015 |
| CN | 112236812 | 1/2021 |
| DE | 19826171 | 10/1999 |
| DE | 10116166 | 10/2002 |
| EP | 0206746 B1 | 8/1992 |
| EP | 0541646 | 1/1995 |
| EP | 0580579 | 6/1998 |
| EP | 0698298 | 2/2000 |
| EP | 0932523 | 6/2000 |
| EP | 0666012 | 11/2002 |
| EP | 2509069 | 10/2012 |
| EP | 2814267 B1 | 10/2016 |
| ES | 2218599 | 10/1998 |
| ES | 2249788 | 10/1998 |
| ES | 2219949 | 8/1999 |
| GB | 2003707 A | 3/1979 |
| GB | 2320393 | 12/1996 |
| HK | 1253783 | 1/2021 |
| IL | 245250 | 12/2020 |
| JP | 3150910 | 6/1991 |
| JP | 7106876 | 4/1995 |
| JP | 2001509985 | 7/2001 |
| JP | 2005500768 | 1/2005 |
| JP | 2005354297 | 12/2005 |
| JP | 2011059714 | 3/2011 |
| KR | 1020040022442 | 3/2004 |
| SU | 1319288 | 6/1987 |
| TW | 401713 | 8/2000 |
| TW | I722529 | 3/2021 |
| WO | WO 9219080 | 10/1992 |
| WO | WO 1993011637 | 6/1993 |
| WO | WO 9321743 | 10/1993 |
| WO | WO 9427331 | 11/1994 |
| WO | WO 9514296 | 5/1995 |
| WO | WO 9531805 | 11/1995 |
| WO | WO 9535628 | 12/1995 |
| WO | WO9535628 | 12/1995 |
| WO | WO 9601547 | 1/1996 |
| WO | WO 9611465 | 4/1996 |
| WO | WO 9708847 | 3/1997 |
| WO | WO 9709698 | 3/1997 |
| WO | WO 9709840 | 3/1997 |
| WO | WO 9709841 | 3/1997 |
| WO | WO 9709842 | 3/1997 |
| WO | WO 9709843 | 3/1997 |
| WO | WO 9709844 | 3/1997 |
| WO | WO 9709845 | 3/1997 |
| WO | WO 9709846 | 3/1997 |
| WO | WO 9709848 | 3/1997 |
| WO | WO 9709849 | 3/1997 |
| WO | WO 9709852 | 3/1997 |
| WO | WO 9709853 | 3/1997 |
| WO | WO 9709854 | 3/1997 |
| WO | WO 9709855 | 3/1997 |
| WO | WO 9709856 | 3/1997 |
| WO | WO 9709857 | 3/1997 |
| WO | WO 9709858 | 3/1997 |
| WO | WO 9709859 | 3/1997 |
| WO | WO 9709861 | 3/1997 |
| WO | WO 9709862 | 3/1997 |
| WO | WO 9717818 | 5/1997 |
| WO | WO 9717820 | 5/1997 |
| WO | WO 9813942 | 4/1998 |
| WO | WO 9816409 | 4/1998 |
| WO | WO 9828942 | 7/1998 |
| WO | WO 9831188 | 7/1998 |
| WO | WO 9834320 | 8/1998 |
| WO | WO 9839947 | 9/1998 |
| WO | WO 9842536 | 10/1998 |
| WO | WO 9843464 | 10/1998 |
| WO | WO 9852381 | 11/1998 |
| WO | WO 9852383 | 11/1998 |
| WO | WO 9853638 | 11/1998 |

(56) References Cited

FOREIGN PATENT DOCUMENTS

| | | |
|---|---|---|
| WO | WO 9902012 | 1/1999 |
| WO | WO 9908479 | 2/1999 |
| WO | WO 9911490 | 3/1999 |
| WO | WO 9912387 | 3/1999 |
| WO | WO 9913684 | 3/1999 |
| WO | WO 9921397 | 4/1999 |
| WO | WO 9935636 | 7/1999 |
| WO | WO 9935883 | 7/1999 |
| WO | WO 9937121 | 7/1999 |
| WO | WO 9938155 | 7/1999 |
| WO | WO 9941939 | 8/1999 |
| WO | WO 9952322 | 10/1999 |
| WO | WO 9952324 | 10/1999 |
| WO | WO 9956497 | 11/1999 |
| WO | WO 9962294 | 12/1999 |
| WO | WO 9965274 | 12/1999 |
| WO | WO 0001264 | 1/2000 |
| WO | WO 0002417 | 1/2000 |
| WO | WO 0007408 | 2/2000 |
| WO | WO 0007409 | 2/2000 |
| WO | WO 0013464 | 3/2000 |
| WO | WO 0015003 | 3/2000 |
| WO | WO 0033612 | 6/2000 |
| WO | WO 0033613 | 6/2000 |
| WO | WO 03104924 | 12/2003 |
| WO | WO 2006020427 | 2/2006 |
| WO | WO 2007092420 | 8/2007 |
| WO | WO 2008067454 | 6/2008 |
| WO | WO 2009070797 | 6/2009 |
| WO | WO 2009102750 | 8/2009 |
| WO | WO 2009114746 | 9/2009 |
| WO | WO 2009155057 | 12/2009 |
| WO | WO2009155057 | 12/2009 |
| WO | WO 2010027705 | 3/2010 |
| WO | WO 2010051354 | 5/2010 |
| WO | WO2010051354 | 5/2010 |
| WO | WO2010138311 | 12/2010 |
| WO | WO 2011081965 | 7/2011 |
| WO | WO 2012134399 | 10/2012 |
| WO | WO2012154823 | 11/2012 |
| WO | WO 2013055394 | 4/2013 |
| WO | WO 2013076223 | 5/2013 |
| WO | WO2013077918 | 5/2013 |
| WO | WO 2014201103 | 12/2014 |
| WO | WO 2015061393 | 4/2015 |
| WO | WO 2015077681 | 5/2015 |
| WO | WO 2016019263 | 2/2016 |
| WO | WO 2016022422 | 2/2016 |
| WO | WO 2016144861 A1 | 9/2016 |
| WO | WO 2019051075 | 3/2019 |
| WO | WO2019200119 | 10/2019 |
| WO | WO 2020028833 | 2/2020 |
| WO | WO2020132060 | 6/2020 |
| WO | WO2021126981 | 6/2021 |

OTHER PUBLICATIONS

Stephan Peus et al. "Natürliche Hören mite künstlichem Kopf", Funkschau—Zeitschrift für elektronische Kommunikation, Dec. 31, 1983, pp. 1-4, XP055451269. Web: https://www.neumann.com/?lang-en&id=hist_microphones&cid=ku80_publications.

Jeffs et al., Dynamics Processors—Technology & Applications Tips, Rane Note 155, Rane Corporation, Sep. 2005, pp. 1-28, Sep. 1, 2005.

\* cited by examiner

AUDIO ENHANCED HEARING PROTECTION SYSTEM

BACKGROUND OF THE INVENTION

Field of the Invention

An audio enhanced hearing protection system includes an ambient noise reduction assembly to substantially decrease the level of environmental noise to which a user is subjected, an audio input assembly including one or more environmental microphones to realistically reproduce an aural landscape to a user, a digital signal processing assembly to transform raw audio signals prior to transmission of processed audio signals to a user.

Description of the Related Art

In certain industries and recreational activities, persons may be in environments in which they are exposed to extremely high levels of continuous ambient noise. Ambient noise can exceed sustained levels of 120 decibels (dB) or more. Just a few examples of high noise level environments include stock car racing events, airports, mining operations, and musical concerts in large arenas and stadiums, just to name a few. Without some form of hearing protection, sustained exposure to extremely high levels of ambient noise can result in serious hearing loss, which in some cases may be permanent, for persons in such environments. Unfortunately, often times hearing protection makes it difficult, if not impossible, for a wearer to communicate with other persons in such high noise level environments. Furthermore, hearing protection devices also severely degrade situational awareness by blocking or severely limiting the environmental audio signals which reach a wearer's ears.

Among the drawbacks to the current state of the art hearing protection devices is that the microphone(s) utilized to capture environmental audio signals for use in reproducing the outside world sounds for a user tend not to be a realistic representation of the aural landscape of the particular high noise level environment. This is due in part to the fact that the frequency response suffers greatly and is very unnatural, for example, the directionality of environmental sounds is limited or non-existent, especially in terms of discerning front from back and/or up from down. There are also hard limiters built into most state of the art devices which cause all sound to cut whenever a loud, transient sound occurs.

One attempt to overcome the aforementioned problems includes electronic hearing assist devices having electronic voice communications as well as externally mounted microphone assemblies to re-introduce environmental sounds at safer noise levels. However, the current state of the art for such devices is far from perfect.

Another significant drawback exhibited by current state of the art hearing protection devices is that voice communication signals tend to be heavily filtered and distorted such that it is oftentimes unintelligible to a person receiving a voice communication.

The current state of the art hearing protection devices tend to consist exclusively of either in-ear plugs/buds or external earmuffs. Unfortunately, neither of these devices in and of themselves always provide enough hearing protection. However, wearing both current state of the art in-ear and external earmuffs at the same time, though increasing overall hearing protection, severely diminishes the quality of communications and environmental awareness.

As such, it would be highly beneficial to provide an audio enhanced hearing protection system which realistically recreates the aural landscape of a particular high noise level environment in which a user is present. It would be further beneficial to provide an audio enhanced hearing protection system which includes a noise reduction assembly that provides a substantial reduction in the ambient environmental noise level, i.e., 50 dBs or more. Such a noise reduction assembly may include both primary and secondary noise reduction units. Another advantage may be realized by providing an audio enhanced hearing protection system which includes a voice communication receiver to pick up voice communication audio signals from a user. Yet another advantage may be realized by providing an audio enhanced hearing protection system having a digital signal processing assembly that increases the level of speech intelligibility of voice communications transmitted to a user.

SUMMARY OF THE INVENTION

The present invention is directed to an audio enhanced hearing protection system. In one embodiment, an audio enhanced hearing protection system includes an ambient noise reduction assembly comprising at least one primary noise reduction unit. In another embodiment, an ambient noise reduction assembly also includes a secondary noise reduction unit, and in still one further embodiment, an ambient noise reduction assembly comprises at least one primary noise reduction unit interconnected to at least one secondary noise reduction unit such that the ambient noise reduction assembly provides for a substantial reduction in the ambient noise level which reaches a user's ears.

An audio enhanced hearing protection system in accordance with the present invention also includes an audio input assembly comprising one or more environmental microphones positioned so as to receive environmental audio signals from the aural landscape surrounding a user. In at least one further embodiment, one or more environmental microphone of an audio enhanced hearing protection assembly in accordance with the present invention is mounted in a microphone manifold, wherein the microphone manifold is configured to at least partially mimic a human ear to mechanically filter the environmental audio signals.

A digital signal processing assembly is included in at least one embodiment of an audio enhanced hearing protection system in accordance with the present invention. A digital signal processing assembly includes a digital processer to transform environmental audio signals into processed audio signals. In at least one embodiment, a digital processer limits extremely loud environmental sounds to safe levels for the user without loss or artifacting of the environmental sounds themselves.

An audio enhanced sound protection system in accordance with at least one embodiment of the present invention also includes an audio output assembly including one or more speakers to transmit the processed audio signals to a user.

Processed audio signals from a digital signal processing assembly in accordance with the present invention may be combined in any number of different ways allowing the present system to be effectively utilized to any of a variety of environments having high levels of ambient noise.

In one embodiment, the present audio enhanced hearing protection system provides a user a level control with which the mix between environmental audio signals and voice communication audio signals may be continually adjusted.

In another embodiment, environmental audio signals may be switched on by use of a momentary switch to allow for a push-to-talk type of feature for communicating with other persons in a high level ambient noise environment. In such an embodiment, the voice communication audio signals may always be on, while the environmental audio signals are muted.

In one further embodiment, both environmental audio signals and voice communication audio signals are activated, but the digital processer is programmed with a threshold for automatic mute and unmute of the environmental audio signals.

In yet another embodiment, the voice communication audio signals may be combined with or replaced by an additional wired or wireless audio signals designed to carry entertainment, such as music. In such an embodiment, the digital signal processing assembly is programmed for multiple modes so as to provide speech intelligibility for voice communication audio signals or digital audio enhancement for audio signals comprising entertainment. If the audio signals remain in separate channels, they could be processed separately by the digital signal processing assembly for their individual intended purposes.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
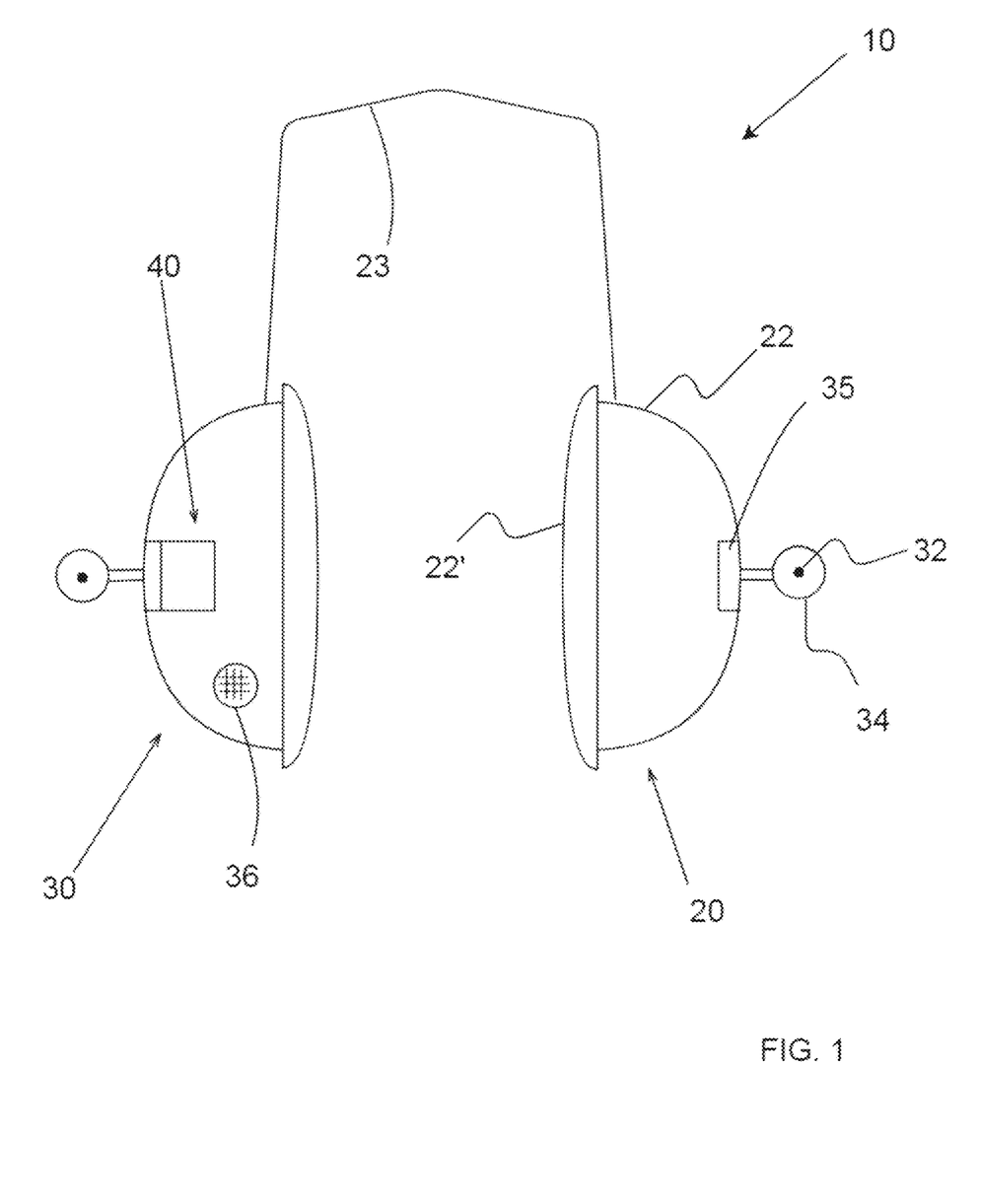
FIG. 1 is a front elevation of one illustrative embodiment of an audio enhanced hearing protection system in accordance with the present invention.

As stated above, the present invention is directed to an audio enhanced hearing protection system generally as shown at 10 throughout the figures. The illustrative embodiment of FIG. 1 presents a front view of an audio enhanced hearing protection system 10 in accordance with the present invention. As may be seen from FIG. 1, an audio enhanced hearing protection system 10 includes an ambient noise reduction assembly 20. As further shown in the illustrative embodiment of FIG. 1, the ambient noise reduction assembly 20 includes a pair of primary noise reduction unite 22 each corresponding to one of a user's ears. Also shown in FIG. 1 is a support member 23 which, in at least one embodiment, connects the primary noise reduction units 22 to one another. The support member 23 further facilitates disposition of the present audio enhanced hearing protection system 10 into an operative orientation relative to a user's head and ears.

Each primary noise reduction unit 22 in accordance with the present invention is configured to surround a corresponding one of a user's ear to significantly reduce the level of ambient noise which reaches a user's ears. In at least one embodiment, a primary noise reduction unit 22 includes a seal 22'. As may be best seen in the illustrative embodiment of FIG. 3, a seal 22' comprises a circumferential configuration such that when an audio enhanced hearing protection system 10 is disposed into an operative orientation relative to a user's ears, the seal 22' of the primary noise reduction unit 22 may be positioned over and in a completely surrounding orientation relative to a user's outer ear. In accordance with at least one embodiment of the present invention, the primary noise reduction units 22 disposed in an operative orientation over a user's ears will reduce the level of ambient noise which reaches the user's ears by at least 30 decibels (dBs).

In accordance with at least one embodiment of an audio enhanced hearing protection system 10 of the present invention, an ambient noise reduction assembly 20 further comprises at least one secondary noise reduction unit 24. Looking to the illustrative embodiments of FIGS. 3 and 4, an ambient noise reduction assembly 20 includes at least one secondary noise reduction unit 24 which is interconnected to a corresponding primary noise reduction unit 22 via an interconnect 26. In at least one embodiment, a secondary noise reduction unit 24 comprises an earbud configured to be inserted into the opening of a user's ear canal. As will be appreciated by those of skill in the art, an earbud can be constructed of any of a variety of pliable materials including foam, silicone, gels, etc., such that the earbud substantially conforms to and fully seals off the opening of the user's ear canal.

Figure 3:
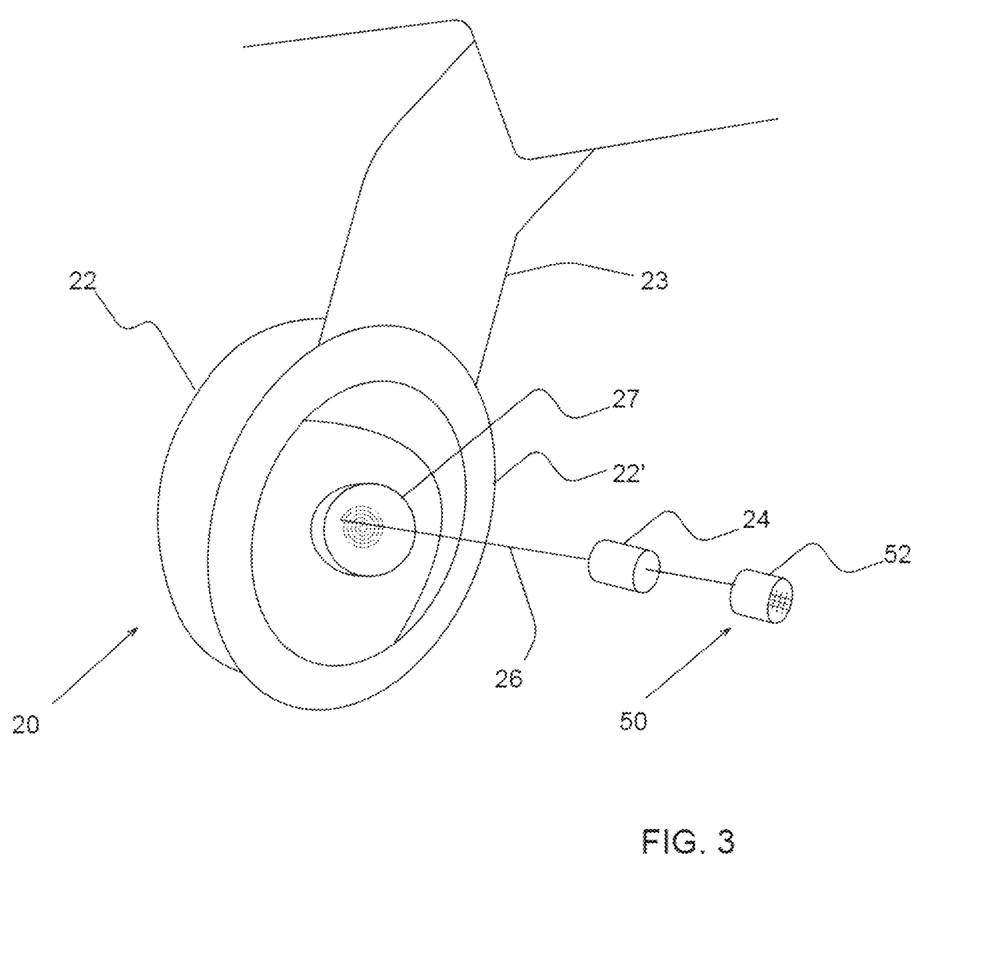
FIG. 3 is partial interior perspective view of a portion of an audio enhanced hearing protection system in accordance with the present invention.
Figure 4:
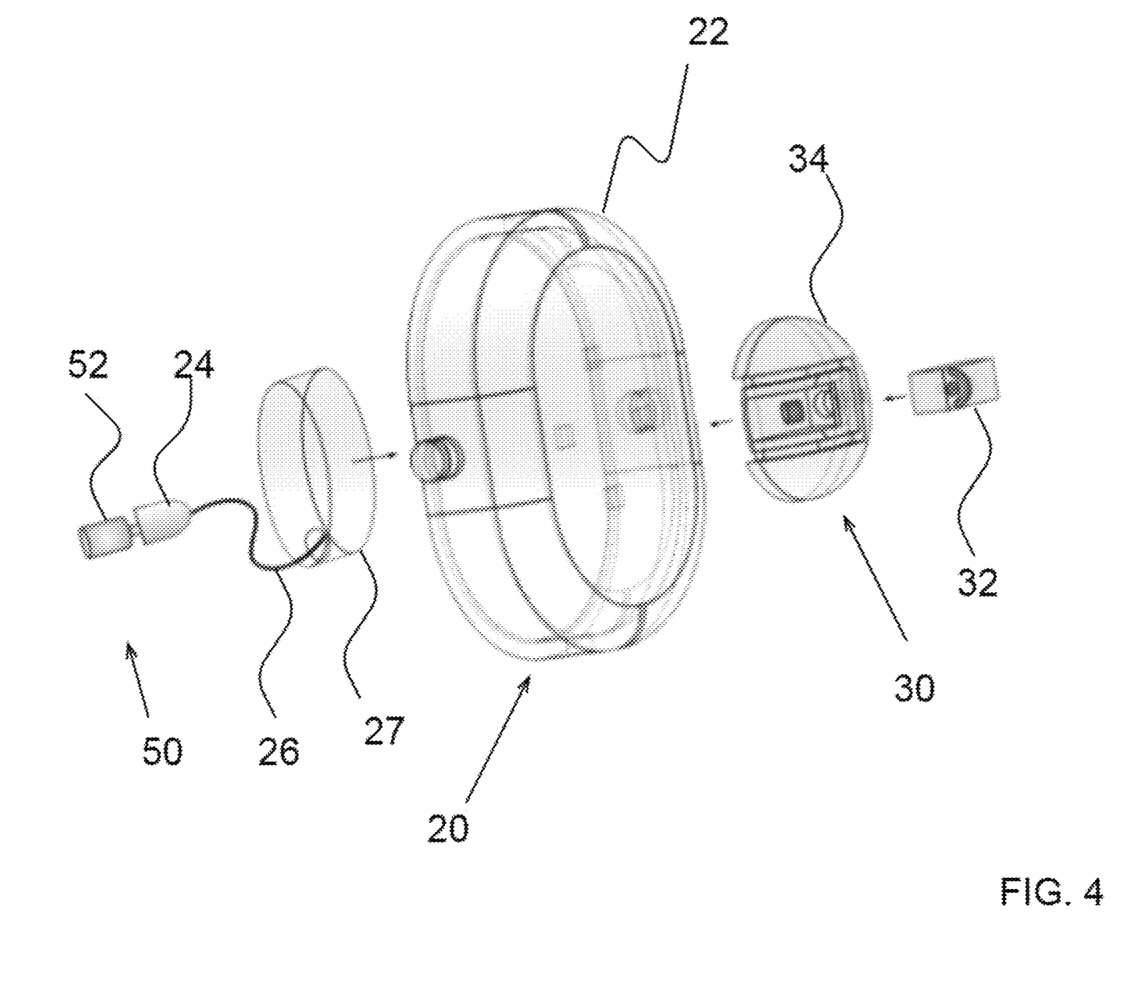
FIG. 4 is an exploded perspective view of a portion of an audio enhanced hearing protection system in accordance with the present invention.

With continued reference to the illustrative embodiments of FIGS. 3 and 4, the secondary noise reduction unit 24 is interconnected to a corresponding primary noise reduction unit 22 via an adjustable interconnect 27. More in particular, in at least one embodiment, an adjustable interconnect 27 comprises a take-up reel onto which interconnect 26 is retracted when a primary noise reduction unit 22 is disposed into an operative position over a user's ear. In at least one embodiment, adjustable interconnect 27 comprises a ratcheting take-up reel which is attached to an interior portion of a primary noise reduction unit 22. In one other embodiment, an adjustable interconnect 27 comprises a spring-loaded take-up reel attached to an interior portion of a primary noise reduction unit 22. As such, a secondary noise reduction unit 24 may be extended outwardly from the primary noise reduction unit 22 via interconnect 26, for ease of insertion of the secondary noise reduction unit 26, i.e., an earbud, into the opening of a user's ear canal.

Once a secondary noise reduction unit 24 is properly positioned into an operative orientation in the opening of a user's ear canal, interconnect 26 retracts onto the take-up reel of adjustable interconnect 27 as the corresponding primary noise reduction unit 22 is operatively positioned over and around the user's outer ear. By virtue of the adjustable interconnect 27, interconnect 26 remains entirely within the interior of primary noise reduction unit 22 thereby eliminating interference with seal 22' which, as will be appreciated by those of skill in the art, could prevent the primary noise reduction unit 22 from providing the maximum level of noise reduction. Further, disposition of interconnect 26 around a take-up spool of adjustable interconnect 27 avoids simply bunching the interconnect 26 up inside of the primary noise reduction unit 22, thus enhancing the comfort of a user wearing the present audio enhanced hearting protection system 10.

In accordance with at least one embodiment of the present invention, a secondary noise reduction unit 24 disposed in an operative orientation in the opening of a user's ear canal will reduce the level of ambient noise which reaches a user's ears by at least 20 dBs. Furthermore, when both the primary noise reduction units 22 and the secondary noise reduction units 24 of an ambient noise reduction assembly 20 are disposed in their respective operative orientations on a user, the level of ambient noise which reaches a user's ears is substantially reduced by at least 50 dBs.

Figure 2:
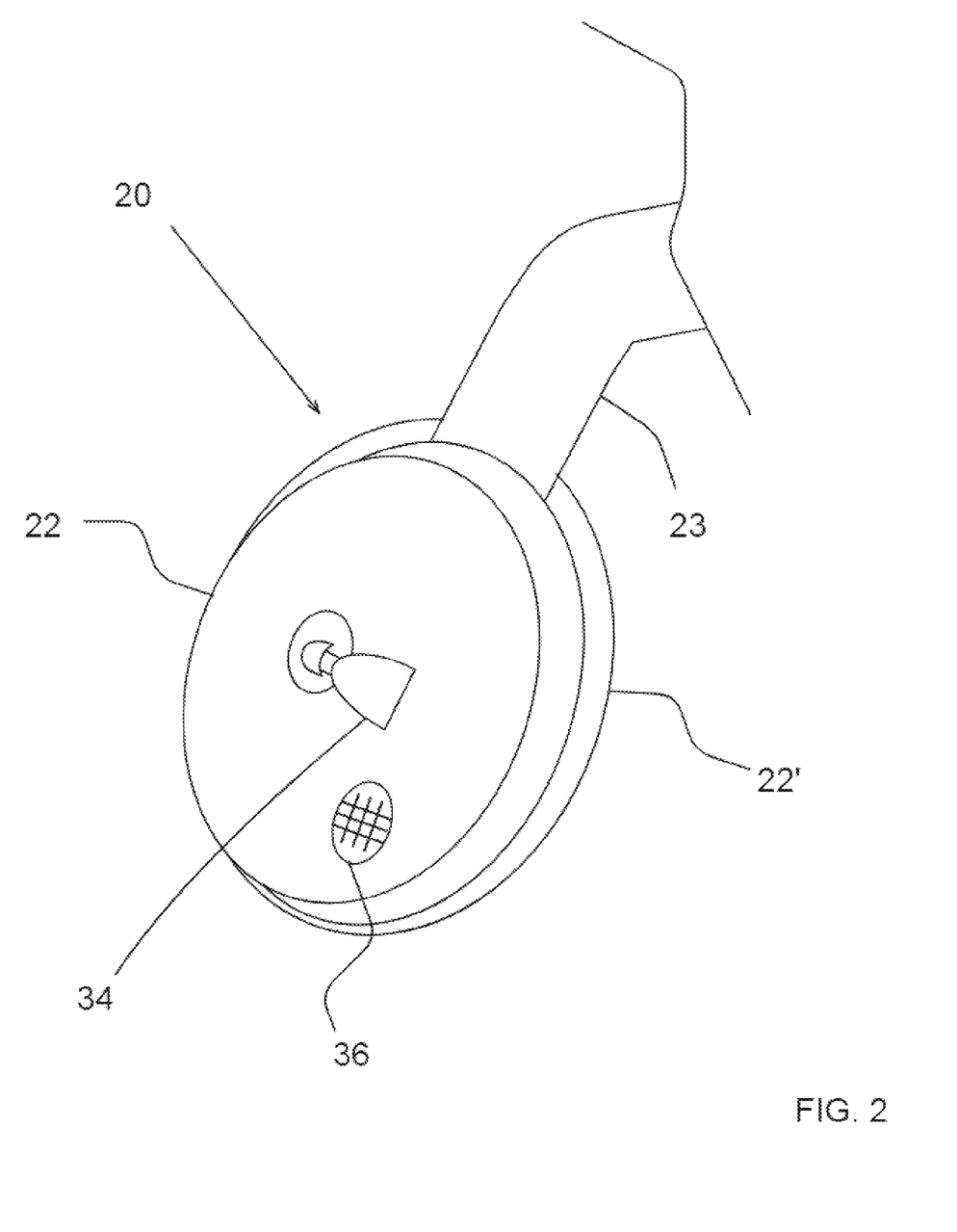
FIG. 2 is an exterior perspective view of a portion of an audio enhanced hearing protection system in accordance with the present invention.

With reference once again to the illustrative embodiment of FIG. 1, an audio enhanced hearing protection system 10 in accordance with the present invention also includes an audio input assembly 30. An audio input assembly 30 in accordance with the present invention includes at least one environmental microphone 32. In at least one embodiment, and as shown in FIG. 1, an audio input assembly 30 includes a plurality of environmental microphones 32. As further shown in FIG. 1, an audio input assembly 30 in accordance with the present invention includes an environmental microphone 32 installed in a microphone manifold 34 which is mounted to each primary noise reduction unit 22. As may also be seen from FIGS. 1 and 2, in at least one embodiment, environmental microphones 32 are mounted to each primary noise reduction unit 22 such that the environmental microphones 32 are facing forward in the direction in which a user wearing the present audio enhanced hearing protection system 10 is looking. When a pair of environmental microphones 32 are housed in corresponding microphone manifolds 34 which are mounted to an ambient noise reduction assembly 20 in a binaural configuration, such as is shown by way of example in the illustrative embodiment of FIG. 1, the audio input assembly 30 of the present invention will provide a minimum of 20 degrees of resolution in any direction relative to a user's head.

In accordance with one embodiment of the present invention, a microphone manifold 34 is configured to at least partially mimic a human ear. As such, a microphone manifold 34 in accordance with the present invention serves to mechanically filter environmental audio signals 33 thereby allowing a realistic reproduction of the environmental audio signals 33 which at least partially comprise the aural landscape of the environment in which a user finds himself or herself.

In accordance with at least one embodiment of the present invention, an audio input assembly 30 further comprises at least one voice communication receiver 36. As will be appreciated by those of skill in the art, a voice communication receiver 36 may comprise a hardwired configuration, for example, an in-line microphone such as are commonly incorporated into hardwired headsets and earbuds. In at least one further embodiment, a voice communication receiver 36 may comprise a wireless audio receiver which may, by way of example, comprise a Bluetooth enabled audio receiver. As may be seen from the illustrative embodiments of FIGS. 1 and 2, audio input assembly 30 comprises at least one voice communication receiver 36 mounted to a primary noise reduction unit 22.

An audio enhanced hearing protection system 10 in accordance with the present invention further comprises a digital signal processing assembly 40 which receives a raw audio signal 42 from an audio input assembly 30. As will be appreciated from the foregoing, a raw audio signal input 42 may comprise an environmental audio signal 33 captured by an environmental microphone 32 of an audio input assembly 30. In at least one embodiment, an environmental audio signal 33 captured by an environmental microphone 32 is processed through a preamplifier 35 prior to transmittal to a digital signal processing assembly 40. Alternatively, a raw audio signal input 42 may comprise a voice communication audio signal 37 captured by a voice communication receiver 36 of an audio input assembly 30. In one further embodiment, a raw audio signal 42 may comprise both an environmental audio signal 33 and a voice communication audio signal 37.

Figure 5:
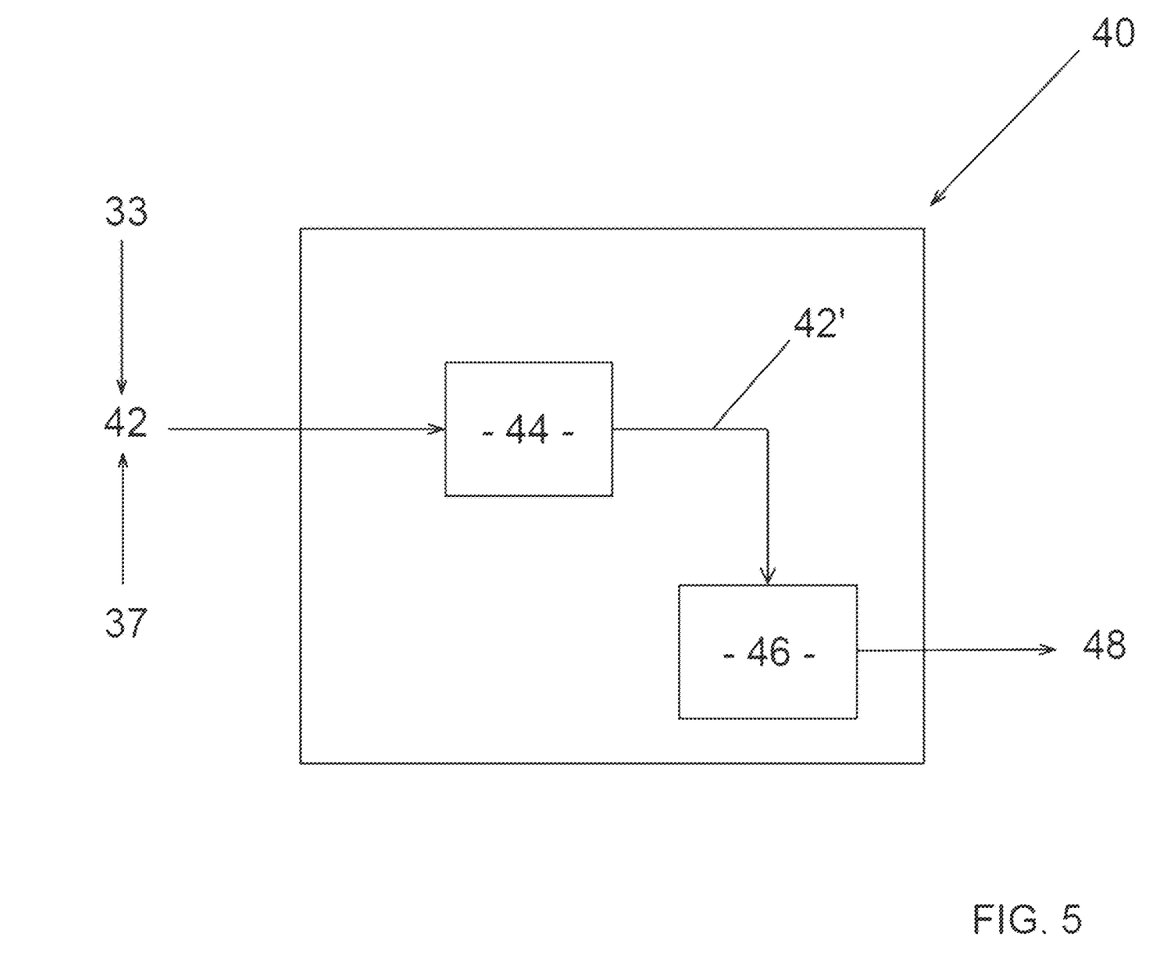
FIG. 5 is a diagrammatic representation of one illustrative embodiment of a digital signal processing assembly of an audio enhanced hearing protection system in accordance with the present invention.

With reference to the illustrative embodiment of FIG. 5, a digital signal processing assembly 40 receives a raw audio signal 42 which, as stated above, may comprise an environmental audio signal 33, a voice communication audio signal 37, or a combination of the two. In at least one embodiment, a digital signal processing assembly 40 in accordance with the present invention comprises an amplifier 44 to boost the amplitude of raw audio signals 42 prior to processing, as well as to drive one or more speakers 52, as discussed further below. Looking further to the illustrative embodiment of FIG. 5, a digital signal processing assembly 40 further comprises a digital processor 46. In accordance with at least one embodiment of the present invention, a digital processor 46 receives an amplified raw audio signal 42' and transforms the amplified raw audio signal 42' into a processed audio signal 48 for transmission to a user's ears via an audio output assembly 50, as described hereinafter.

A digital signal processing assembly 40 in accordance with the present invention may be programmed in any of a number of ways. As one example, environmental audio signals 33 obtained from one or more environmental microphones 32 may be processed as described in U.S. Pat. No. 8,160.274, which is directed to a system and method for digital signal processing. Processing environmental audio signals 33 in accordance with the aforementioned method for digital signal processing creates a processed audio signal 48 having superior frequency response control allowing for a natural and realistic representation of the real-world acoustic environment. In addition, the aforementioned method provides for limiting extremely loud transient sounds to safe levels without any loss or without adding artifacts to other environmental sounds. By way of example, if a gun is fired in the proximity of the person who is speaking, the gunshot can be limited to a safe level, while the person's voice is processed to remain at a consistent level. As a result of utilizing the digital signal processing assembly 30 in this manner, the ambient noise reduction assembly 20 of the present invention functions as an active noise reduction assembly 20. In at least one further embodiment, the digital processor 46 is programmed to generate a noise cancelling signal, based on an incoming raw audio signal 42, thereby transforming the ambient noise reduction assembly 20 into an active "noise cancelling" noise reduction assembly 20.

The aforementioned method for digital signal processing is particularly effective when environmental audio signals 33 are obtained from an environmental microphone 32 that is mounted in a microphone manifold 34 as described hereinabove. More in particular, a raw audio signal 42 obtained from an environmental microphone 32 mounted in a microphone manifold 34 can be processed so as to achieve a perfect recreation of the directionality of environmental sounds on all axes of an aural landscape.

For the voice communication audio signals 37, the signal 37 could be processed as described in either U.S. Pat. No. 9,264,004, directed to a system and method for narrow bandwidth digital signal processing, or as described in U.S. Pat. No. 8,160,274, directed to a system and method for digital signal processing, as both are capable of effectively and measurably increasing the intelligibility of human speech.

As before, a raw audio signal 42 may be transformed in any number of different ways into a processed audio signal 48 via a digital signal processing assembly 40 in accordance with the present invention, allowing the present audio enhanced hearing protection system 10 to be effectively utilized in any of a variety of environments having high levels of ambient noise. More in particular, a digital signal processing assembly 40 in accordance with the present invention is programmed to provide increased speech intelligibility from voice communication signals 37 and to convert incoming environmental audio signals 33 into processed audio signals 48 which create a natural, realistic recreation of the aural landscape in the outside world to a user's ears.

In one embodiment, the digital processer 46 of the present audio enhanced hearing protection system 10 includes level controls with which the mix between environmental audio signals 33 and voice communication audio signals 37 may be continually adjusted to optimize processed audio signals 48 transmitted to a user.

In another embodiment, environmental audio signals 33 may be switched on momentary to allow for a push-to-talk type of feature for communicating with other persons in a high level ambient noise environment. In such an embodiment, the voice communication audio signals 37 may always be on, while environmental audio signals 33 are muted until switched on.

In one further embodiment, both environmental audio signals 33 and voice communication audio signals 37 are activated, but the digital processer 46 is programmed with a threshold for automatic mute and unmute of the environmental audio signals 33.

In yet another embodiment, the voice communication audio signals 37 may be combined with or replaced by additional wired or wireless audio signals designed to carry entertainment, such as music. In such an embodiment, the digital signal processing assembly 40 is programmed for multiple modes so as to provide speech intelligibility for voice communication audio signals 37 or digital audio enhancement for audio signals comprising entertainment. If the audio signals remain in separate channels, they could be processed separately by the digital signal processing assembly 40 for their individual intended purposes.

As previously stated, an audio enhanced hearing protection system 10 in accordance with the present invention further comprises an audio output assembly 50 to allow transmittal of processed audio signals 48 from a digital signal processing assembly 40 to a user's ears. An audio output assembly 50 in accordance with the present invention comprises at least one speaker 52 to transmit processed audio signals 48 to a user's ears. With reference to the illustrative embodiments of FIGS. 3 and 4, an audio output assembly 50 comprises at least one speaker 52 which is mounted into a secondary noise reduction unit 24, such as, by way of example only, a pliable earbud. In at least one embodiment, an audio output assembly 50 comprises a pair of speakers 52, each being mounted into a different secondary noise reduction unit 24 corresponding to each of a user's ears.

An interconnect 26 may include or consist of a wire connection to facilitate transmission of processed audio signals 48 from the digital signal processing assembly 40 to the speaker 52. In at least one embodiment, a speaker 52 comprises a wireless audio speaker 52 which, by way of example once again, may comprise a Bluetooth enabled audio speaker 52.

Since many modifications, variations and changes in detail can be made to the described embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. An audio enhanced hearing protection system to be worn by a user comprising:
an ambient noise reduction assembly comprising a pair of primary noise reduction units connected to one another by a support member, and a pair of secondary noise reduction units each adjustably interconnected to a different one of said pair of primary noise reduction units;
an audio input assembly comprising at least two microphone manifolds, said at least two microphone manifolds each housing at least one environmental microphone oriented to face forward in the direction the user is looking and configured to receive environmental audio signals such that said audio input assembly provides a minimum resolution of 20 degrees in any direction relative to the user's head;
a digital signal processing assembly; and
an audio output assembly comprising at least one speaker to transmit processed audio signals.

2. The system as recited in claim 1 wherein said audio input assembly further comprises at least one voice communication receiver to receive a plurality of voice communication audio signals from the user.

3. The system as recited in claim 2 wherein said digital signal processing assembly comprises a digital processer configured to transform said plurality of voice communications audio signals into a plurality of processed audio signals, wherein said digital processer increases speech intelligibility of voice communications.

4. The system as recited in claim 1 wherein said ambient noise reduction assembly is configured to reduce ambient noise levels by at least 50 decibels.

5. The system as recited in claim 1 wherein said ambient noise reduction assembly is passive.

6. The system as recited in claim 1 wherein said ambient noise reduction assembly is active.

7. The system as recited in claim 1, wherein each of said at least two microphone manifolds is further configured to at least partially mimic a human ear to mechanically filter said environmental audio signals.

8. The system as recited in claim 1, wherein each of said at least two microphone manifolds is mounted to said ambient noise reduction assembly in a binaural configuration.

9. The system as recited in claim 1, wherein said digital signal processing assembly is configured to transform a raw audio signal into said processed audio signals.

10. The system as recited in claim 9, wherein said raw audio signal comprises said environmental audio signals.

11. The system as recited in claim 1, wherein said audio input assembly further comprises a preamplifier.

12. The system as recited in claim 1, wherein said pair of primary noise reduction units are configured to reduce ambient noise levels by at least 30 decibels.

13. The system as recited in claim 1, wherein said pair of secondary noise reduction units are configured to reduce ambient noise levels by at least 20 decibels.

\* \* \* \* \*